United States Patent [19]

Tomalia et al.

[11] Patent Number: 4,529,803

[45] Date of Patent: Jul. 16, 1985

[54] PROCESS FOR PREPARING IMIDAZOLINIUM COMPOUNDS

[75] Inventors: Donald A. Tomalia; Fredric L. Buchholz, both of Midland, Mich.

[73] Assignee: The Dow Chemical Company, Midland, Mich.

[21] Appl. No.: 227,830

[22] Filed: Jan. 23, 1981

Related U.S. Application Data

[62] Division of Ser. No. 103,832, Dec. 12, 1979, Pat. No. 4,267,350.

[51] Int. Cl.³ .................... C07D 233/22; C07D 233/18
[52] U.S. Cl. ..................................................... 548/354
[58] Field of Search ......................................... 548/354

[56] References Cited

U.S. PATENT DOCUMENTS

| | | | |
|---|---|---|---|
| 2,794,765 | 6/1957 | Albrecht | 424/273 R |
| 2,874,074 | 2/1959 | Johnson | 548/354 X |
| 3,003,969 | 10/1961 | Albrecht | 252/142 |
| 3,033,704 | 5/1962 | Sherril et al. | 548/354 X |
| 3,514,399 | 5/1970 | Robinson | 548/354 X |
| 3,681,241 | 8/1972 | Rudy | 252/8.75 |
| 3,922,282 | 11/1975 | Shah | 424/273 R |
| 4,127,489 | 11/1978 | Pracht et al. | 252/8.8 |

FOREIGN PATENT DOCUMENTS

| | | | |
|---|---|---|---|
| 4-950 | 10/1979 | European Pat. Off. | 548/354 |
| 40-70307 | 6/1965 | Japan | 548/354 |
| 1407134 | 9/1975 | United Kingdom | 548/354 |

OTHER PUBLICATIONS

Isagulyants, V., et al., *ZH. Prik. Khim.*, 43(9), 2120–2122, (1970).
Isagulyants et al., *Chem. Abst.*, 1971, vol. 74, No. 3552v.
March, J., *Advanced Organic Chemistry: Reactions, Mechanisms and Structure*, N.Y., McGraw-Hill, 1968, p. 336 and 2nd Edition, 1977, p. 386.

*Primary Examiner*—Richard A. Schwartz
*Attorney, Agent, or Firm*—Michael L. Glenn; Paul D. Hayhurst

[57] ABSTRACT

A novel imidazolinium salt is prepared by (1) reacting N-aminoalkyl-imidazoline, N-hydroxyalkyl-imidazoline, or N-substituted-imidazoline with an α,β-unsaturated ester of a carboxylic acid, (2) reacting the resulting ester imidazoline with a primary or secondary amine and (3) quaternizing the resulting amido imidazoline product by reacting it with an alkylating agent. This imidazolinium salt is useful as a fabric softening agent.

6 Claims, No Drawings

PROCESS FOR PREPARING IMIDAZOLINIUM COMPOUNDS

CROSS-REFERENCE TO RELATED APPLICATION

This application is a division of my application Ser. No. 103,832 filed Dec. 12, 1979, U.S. Pat. No. 4,267,350.

BACKGROUND OF THE INVENTION

This invention relates to novel imidazolinium salts. Specifically, these compounds are imidazolinium salts which bear at least one

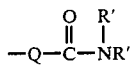

group, wherein each $R'$ is hydrogen or a hydrocarbyl radical and Q is a divalent, saturated, normal hydrocarbon radical optionally containing no more than two oxygen or secondary amine moieties.

There exist myriad examples in the literature of imidazolinium salts useful as cationic surfactants and/or fabric conditioning agents. U.S. Pat. No. 4,127,489 discloses a process for making imidazolinium salts bearing a

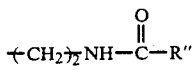

group, wherein $R''$ is a $C_{10}$–$C_{22}$ aliphatic or cycloaliphatic hydrocarbon moiety. U.S. Pat. Nos. 2,874,074 and 3,681,241 also describe imidazolinium salts useful as fabric conditioning agents.

The literature also discloses that certain imidazoline compounds are useful as cationic surfactants or dispersants. See, for example, U.S. Pat. Nos. 3,037,029; 3,003,969 and 2,794,765.

SUMMARY OF THE INVENTION

Novel quaternary imidazolinium salts and inner salts have now been discovered which are represented by the formulae I or IA

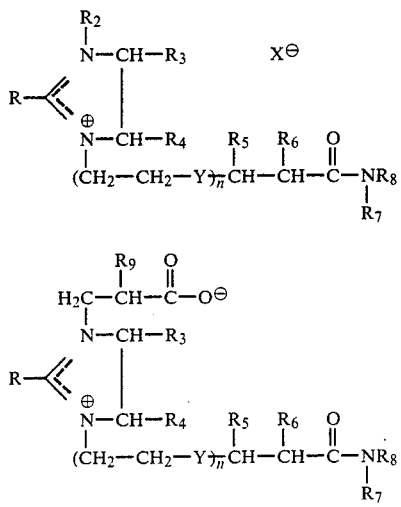

wherein R and $R_7$ are each independently aliphatic, cycloaliphatic or aralkyl hydrocarbon radicals having from 1 to 22 carbon atoms, with the proviso that either R or $R_7$ is an aliphatic radical having 8 to 22 carbon atoms; $R_2$ is an alkyl or aralkyl having from 1 to 8 carbon atoms; $R_3$ and $R_4$ are each independently hydrogen, $C_1$–$C_4$ alkyl or $C_1$–$C_4$ hydroxyalkyl; $R_6$ and $R_8$ are each independently hydrogen or a $C_1$–$C_4$ alkyl; $R_5$ is hydrogen, methyl or

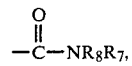

$R_7$ and $R_8$ having the aforementioned meanings; $R_9$ is hydrogen or methyl; Y is the divalent radical —O— or —NH—; X is an anion; and n is the integer 0, 1 or 2, with the proviso that if n is 2, then Y is —NH—.

The novel quaternary imidazolinium salts are useful as corrosion inhibitors and cationic surfactants. These salts are particularly efficacious as fabric softening agents.

DETAILED DESCRIPTION OF THE INVENTION

The process to form the desired imidazolinium salt involves four steps: imidazoline formation, Michael Addition to the imidazoline, amidation and quaternization. All of these reactions are individually known in the art.

A. Formation of the Imidazoline

The imidazoline precursor for the desired imidazoline salt has the formula

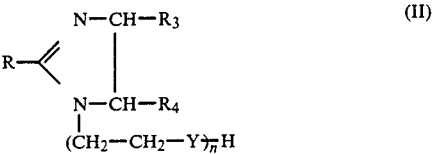

Methods for preparing these imidazolines are well-known in the art. This precursor is conveniently prepared by reacting ethylene polyamine of the formula

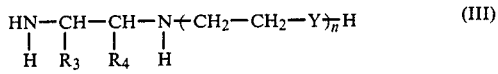

wherein $R_3$, $R_4$, Y and n have the aforementioned meanings, with an acylating reactants, such as a carboxylic acid, ester or acid chloride, having the acyl group

wherein R has the aforementioned identity. This reaction proceeds efficiently at elevated temperatures, generally from about 100° C. to about 250° C., with the evolution of water which is removed by distillation during the course of the reaction. To facilitate the reaction, reduced pressure can be advantageously employed.

Normally, essentially equimolar quantities of the reactants are employed, but an excess of either reactant can operably be present. The progress of the reaction can be monitored by the amount of water recovered in the distillate. Two moles of water are generated for each mole of imidazoline formed, one mole of water being produced in the condensation reaction to an amide and a second mole of water being produced in the cyclodehydration reaction to the imidazoline. Preferably, the reactants are substantially completely (greater than 90 mole percent) converted to the imidazoline. The imidazoline product can be readily recovered by distillation at reduced pressure to remove the more volatile unreacted reactants and impurities as necessary.

The preferred acylating reactants are fatty acids or mixtures thereof having an aliphatic group of from 9 to 23 carbon atoms, so that R has from 8 to 22 carbon atoms. Examples of such fatty acids include lauric, oleic, decanoic, undecanoic, stearic, linoleic, palmitic acids and the like. Especially preferred fatty acids are crude mixtures thereof derived from vegetable or animal oils, such as tall oil, soybean oil or coconut oil. Alkyl esters of the aforementioned fatty acids and the naturally occurring glyceride esters are also operable.

The polyamine reactant is preferably ethylenediamine, diethylenetriamine, linear triethylenetetraamine or aminoethylethanolamine, i.e., $R_3$ and $R_4$ in the compound of formula III are each hydrogen. More preferably, the polyamine reactant is diethylenetriamine or aminoethylethanolamine. The most preferred polyamine reactant is aminoethylethanolamine.

B. Michael Addition

The imidazoline precursor represented by formula II is reacted with an $\alpha,\beta$-unsaturated carboxylic acid ester (IV), as illustrated by the following equation:

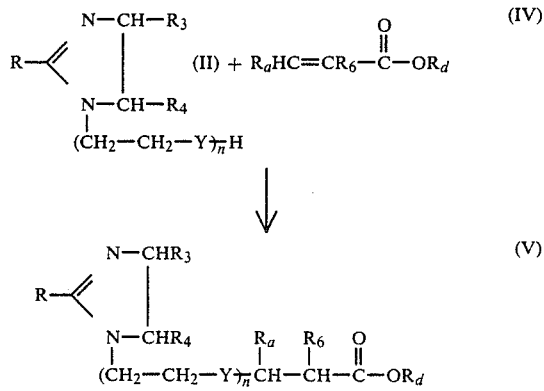

wherein $R_a$ is hydrogen, methyl or

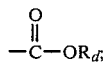

$R_d$ is a $C_1$–$C_4$ alkyl; and the other symbols have the aforementioned identities.

The reaction between the imidazoline of formula II and the unsaturated ester of formula IV occurs rapidly at room temperature (20° C.) or above in a liquid reaction medium. If the imidazoline formation is substantially complete, the compound of formula IV can be introduced directly into the post-reaction mixture from Step A. Otherwise a prior distillation of this post-reaction mixture may be necessary. It is generally advantageous to maintain the reaction temperature at less than 100° C. It is preferred that the reaction be carried out in a neat liquid medium, with agitation at least until the solution becomes homogeneous. The reaction is preferably performed under an inert gas atmosphere (e.g. nitrogen). Typically, equimolar quantities of the reactants are employed. Although an excess of either reactant is operable, this excess must be removed by distillation from the product and therefore, is not desirable. The reaction is usually exothermic and this assists in maintaining a reaction temperature which promotes rapid reaction.

The reactant of formula IV is preferably methyl acrylate, ethyl acrylate, propyl acrylate, butyl acrylate, methyl methacrylate, or ethyl methacrylate. More preferably, this reactant is methyl acrylate, ethyl acrylate or methyl methacrylate. The compound of formula I can be conveniently recovered by distillation of the more volatile components of the reaction mixture, as necessary.

C. Amidation

The imidazoline represented by formula V is reacted with a primary or secondary amine of the formula $H-NR_7R_8$, wherein the symbols have the aforementioned identities, to produce an imidazoline represented by the formula

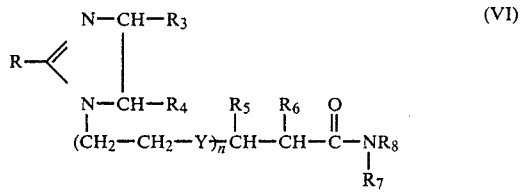

Preferably, $R_8$ is hydrogen and $R_7$ is a $C_8$–$C_{22}$ aliphatic group. If R in formula V is not a $C_8$–$C_{22}$ aliphatic group, then $R_7$ must be a $C_8$–$C_{22}$ aliphatic group.

The amidation reaction proceeds efficiently at elevated temperatures, generally from about 100° C. to about 250° C., with the evolution of a lower alkanol which is removed by distillation during the course of the reaction. To facilitate the reaction, it is best to perform it at reduced pressure. The progress of the reaction can be monitored by the amount of alkanol recovered.

Preferably, stoichiometric quantities of the reactants are employed. Thus, equimolar quantities of the amine and imidazoline are preferably employed, unless $R_a$ in the compound of formula V is an ester moiety, in which case a 2:1 mole ratio of the amine to the imidazoline is preferred. If an excess of either reactant is employed, then the compound of formula VI can be recovered by distillation of the reaction mixture.

D. Quaternization

The compound of formula VI is reacted with an alkylating agent in a known manner to prepare the quaternary imidazolinium salt represented by formulae I or IA. The alkylating agent employed to prepare the salt of formula I can be any one of a number of known agents, such as, methylchloride, ethylbromide, diethylsulfate, dimethylsulfate, hexadecylchloride, and the like, but dimethylsulfate is preferred. In formula I, $R_2$ is an alkyl or aralkyl having from 1 to 8 carbon atoms, preferably a $C_1$–$C_4$ alkyl and X is an anion associated with the alkylating agent, representative anions include chloride, bromide, methylsulfate, ethylsulfate and the like. In formula IA, the salt is an inner salt prepared using acrylic acid or methacrylic acid as the alkylating agent. The quaternary imidazolinium salt represented by formula I is preferred.

Equimolar quantities of the alkylating agent and the imidazoline are operable, but a slight excess of the alkylating agent is preferred to assure maximum quaternization. The excess of the alkylating agent is desirably sufficient to effect a pH in the reaction medium of from about 5 to about 7. The reaction temperature is desirably from about 40° C. to about 80° C. and from about 1 to about 12 hours are necessary to complete the reaction.

Fabric Conditioning Compositions

The imidazolinium salts of formulae I or IA impart superior softening to fabrics, while reducing fabric static charge and retention. The fabric conditioning compositions containing the instant imidazolinium salt are preferably aqueous and contain an effective concentration of the conditioning agent. These compositions preferably contain from about 0.1 to about 10 weight percent, most preferably from about 2 to about 5 weight percent, of the instant salt.

In addition to the subject quaternary imidazolinium salt, the fabric conditioning compositions of the present invention can contain other fabric conditioning agents, such as, antistatic agents, softeners and whiteners. Many of these prior art fabric conditioning agents are described in U.S. Pat. No. 4,127,489, the relevant portions of which are incorporated herein by reference. Other adjuvants can also be employed to advantage in the fabric conditioning composition. These adjuvants include aldehyde preservatives, emulsifiers, thickeners, opacifiers, coloring agents, brighteners, fluorescers, pH adjustment agents and perfumes.

The aqueous fabric conditioning compositions herein can be prepared by adding the instant fabric softening and static control agents to water using conventional techniques. For example, the agent or agents can be heated to form a liquid oily phase, which is then added to water at elevated temperatures with mixing. Adjuvants are added in accordance with methods known in the art. The fabric conditioning composition is then adjusted to a pH of from about 3 to about 9, preferably from about 4.5 to about 7.

Composition Usage

The compositions of the present invention are used in one preferred embodiment in the rinse cycle of the conventional automatic laundry operations. Generally, rinse water has a temperature of from about 15° C. to about 60° C.

When compositions of the present invention are added to the rinse cycle, the fabric conditioning agents are generally present at levels of from about 2 parts per million (ppm) to about 500 ppm, preferably about 10 ppm to about 100 ppm. The concentration levels achieve superior fabric softening and static control.

In general, the invention herein in its fabric conditioning method aspect comprises: (a) washing fabrics in a conventional automatic washing machine with a detergent composition (normally containing a surfactant or mixture of surfactants selected from the group consisting of anionic, nonionic, amphoteric or ampholytic surfactants), (b) rinsing the fabrics, and (c) adding during the rinse stage of the operation the above-described levels of the fabric conditioning agents. Preferably, a final step (d) includes drying the fabrics in an automatic dryer at a temperature of at least about 38° C. This drying stage facilitates spreading of the fabric conditioning materials herein across the fabric surfaces.

The following examples further illustrate the invention. All parts and percentages in the examples are by weight unless otherwise specified.

EXAMPLES 1-10

In a series of ten similar reactions, 1 mole of an imidazoline represented by formula II, wherein n is 0, R is an alkyl identified in Table I, and $R_3$ and $R_4$ are each hydrogen, was charged to a reaction vessel and heated to 90° C. under a nitrogen atmosphere. One mole of methyl acrylate was added to the reaction vessel with stirring at a rate slow enough to maintain a reaction temperature of about 95° C. After the addition of the methyl acrylate was completed, the reaction temperature was maintained at 100° C. for 30 minutes.

One mole of a primary amine, $R_7NH_2$, wherein $R_7$ is tabulated in Table I, was charged to the reaction mixture and the reaction temperature was increased to 180°–200° C. This reaction temperature was maintained, while methanol distilled from the mixture. Infrared spectrophotometric analysis after 3 hours confirmed that no ester remained in the reaction mixture.

The reaction mixture was cooled to 80°–100° C. One mole of dimethylsulfate was added to the stirred reaction mixture at a rate slow enough to maintain a reaction temperature of about 125° C. The reaction mixture was maintained at 130° C. for an additional hour. The product was analyzed by the conventional techniques of infrared spectrophotometric and proton magnetic resonance analysis. The structure for the product represented by formula I was confirmed, wherein n, $R_8$, $R_3$, $R_4$ each have the identities mentioned above; $R_5$ and $R_6$ are each hydrogen, $R_2$ is methyl; $X^\ominus$ is a methylsulfate anion and R and $R_7$ have the identities tabulated in Table I. The desired salt was obtained in essentially quantitative yield in each example.

TABLE I

| Example | R | $R_7$ |
|---|---|---|
| 1 | $-C_2H_5$ | $-C_8H_{17}$ |
| 2 | $-C_2H_5$ | $-C_{12}H_{25}$ |
| 3 | $-C_2H_5$ | $-C_{18}H_{37}$ |
| 4 | $-C_7H_{15}$ | $-C_8H_{17}$ |
| 5 | $-C_7H_{15}$ | $-C_{12}H_{25}$ |
| 6 | $-C_7H_{15}$ | $-C_{18}H_{37}$ |
| 7 | $-C_{11}H_{23}$ | $-C_8H_{17}$ |
| 8 | $-C_{11}H_{23}$ | $-C_{12}H_{25}$ |
| 9 | $-C_{11}H_{23}$ | $-C_{18}H_{37}$ |
| 10 | $-C_{18}H_{37}$ | $-C_{18}H_{37}$ |

EXAMPLE 11

In a manner otherwise identical to Example 2, one mole of acrylic acid was employed as the alkylating agent in place of the dimethylsulfate and reacted for three hours at 130° C. with the imidazoline amide of formula V. The product was found by conventional analytical techniques to correspond to formula IA, wherein n is 0, $R_3$–$R_7$ and $R_9$ are each hydrogen, R is ethyl and $R_8$ is dodecyl.

EXAMPLES 12-14

In a series of three similar reactions, 1 mole of an imidazoline represented by formula II, wherein n is 1; Y is —O—; R is an alkyl or alkenyl identified in Table II and $R_3$ and $R_4$ are each hydrogen, was charged to a reaction vessel and heated to 90° C. under a nitrogen atmosphere. One mole of methyl acrylate was added to the reaction vessel with stirring at a rate slow enough to maintain a reaction temperature of about 95° C. After addition of the methyl acrylate, the reaction temperature was maintained at 100° C. for 3 hours.

One mole of a primary amine, $R_7NH_2$, wherein $R_7$ is an alkyl identified in Table II, was charged to the stirred reaction mixture and the reaction temperature was maintained at 100° C. for 30 minutes. This reaction temperature was maintained, while methanol distilled from the mixture. Infrared spectrophotometric analysis after 3 hours confirmed that no ester remained in the reaction mixture.

The reaction mixture was cooled to 80°–100° C. One mole of dimethylsulfate was added to the stirred reaction mixture at a rate slow enough to maintain a reaction temperature of about 125° C. The reaction mixture was maintained at 130° C. for an additional hour. The structure of the product was elucidated by conventional analytical techniques and can be represented by formula I, wherein R and $R_7$ are each alkyls or alkenyls tabulated in Table II; Y, n, $R_3$, $R_4$ and $R_8$ each have the aforementioned identities; $R_5$ and $R_6$ are each hydrogen; $R_2$ is methyl and $X^\ominus$ is a methylsulfate anion. The desired salt was obtained in essentially quantitative yield in each example.

TABLE II

| Example | R | $R_7$ |
|---|---|---|
| 12 | —$C_{17}H_{35}$ | —$C_{18}H_{37}$ |
| 13 | —$C_{17}H_{33}$ | —$C_{18}H_{37}$ |
| 14 | —$C_{17}H_{33}$ | —$C_4H_9$ |

EXAMPLES 15–17

In a series of three reactions, 0.2 mole of an imidazoline represented by formula II, wherein n is 1; Y is —NH—; R is an alkyl identified in Table III and $R_3$ and $R_4$ are each hydrogen, was reacted with 0.2 mole of methyl acrylate in a manner otherwise identical to Example 1.

Two tenths mole of a primary amine, $R_7NH_2$, was charged to the reaction mixture and the reaction temperature was increased to 200° C. This reaction temperature was maintained while methanol distilled from the mixture. Infrared spectrophotometric analysis after 4 hours confirmed that no ester remained in the reaction mixture.

The reaction mixture was cooled to 90° C. and then 0.2 mole of dimethylsulfate was slowly added with stirring. The stirred reaction mixture was maintained at 100° C. for an additional hour. The product was determined by conventional analytical techniques to correspond to formula I, wherein R and $R_7$ are each alkyls tabulated in Table III; Y, n, $R_3$, $R_4$, and $R_8$ each have the aforementioned identities; $R_5$ and $R_6$ are each hydrogen, $R_2$ is methyl and $X^\ominus$ is a methylsulfate anion.

TABLE III

| Example | R | $R_7$ |
|---|---|---|
| 15 | —$C_2H_5$ | —$C_{12}H_{25}$ |
| 16 | —$C_2H_5$ | —$C_{18}H_{37}$ |
| 17 | —$C_{17}H_{35}$ | —$C_{18}H_{35}$ |

EXAMPLES 18–20

An 8.5 pound load of shirts, sheets, socks and polyester, polyester/cotton and nylon swatches were repeatedly washed in a conventional washing machine with a cup of a typical commercial alkyl benzene sulfonate-based detergent. The temperature of the wash water was 50° C. and the temperature of the rinse water was 25° C. In three of the washes, either 3 or 5 grams of the imidazolinium salt prepared in Example 12 was added in an aqueous solution during the wash or rinse cycle. Between each of the fabric softener tests the laundry was washed three times to remove residual softener. In one wash not embodying this invention, no fabric softening agent was employed.

The laundry was dried after washing in a conventional clothes dryer and the static charge of a shirt and three swatches of cloth was measured with a Simco electrostatic locator at a distance of six inches. The degree of softness of the cloth was subjectively determined by the operator feeling the laundered fabric in each case. The operating parameters and results of these tests are tabulated in Table IV.

TABLE IV

| Example | Agent Loading (grams) | Agent Added | Static (kilovolts) Swatches | Shirt | Softening |
|---|---|---|---|---|---|
| 18 | 5 | Rinse | 0.0–0.5 | 0.8 | Good |
| 19 | 5 | Wash | 2.0–2.5 | 1.0 | Slight |
| 20 | 3 | Rinse | 0.0–0.5 | 1.0 | Moderate |
| Comparative Experiment | None | Not Applicable | 2.0–4.0 | 4.0 | Harsh feel |

EXAMPLE 19

An 8.25 pound load of shirts, sheets, and socks were washed in a conventional washing machine at 45° C. with 0.5 cup of a typical commercial alkyl benzene sulfonate-based detergent. At the beginning of the rinse cycle, a 5.0 gram sample of the imidazolinium salt prepared in Example 17 dissolved in 95 grams of ethanol was added to the laundry. The laundry was dried after washing and the static charge of several shirts was measured with a Simco electrostatic locator at a distance of six inches. The measured static charge of these shirts is tabulated in Table V under "Agent-17".

This laundry was washed three times in the detergent alone to remove the fabric conditioning agent residue, dried and the static charge of the garments was measured once more as described above. The measured static charge is tabulated in Table V under the heading "Comparative Experiment".

The laundry was washed once more and 5.0 grams of the imidazolinium salt prepared in Example 13 dissolved in 95 grams of ethanol was added during the rinse cycle. The laundry was dried and the static charge measured as above. The measured static charge is tabulated in Table V under the heading "Agent-13".

TABLE V

| Shirt No. | Fabric Composition | Static Charge (kilovolts) Agent-17 | Comparative Experiment | Agent-13 |
|---|---|---|---|---|
| 1 | 65% Polyester/35% Cotton | 0.0 | −4.0 | 0.5 |
| 2 | 100% Nylon | 0.0 | 20.0 | 2.0 |
| 3 | 65% Polyester/35% Cotton | 0.5 | −5.0 | −0.5 |
| 4 | 100% Polyester | −1.0 | −10.0 | −0.5 |
| 5 | 100% Nylon | −1.0 | 25.0 | −1.5 |
| 6 | 65% Polyester/35% Cotton | −0.3 | −9.0 | −0.5 |

TABLE V-continued

| Shirt No. | Fabric Composition | Static Charge (kilovolts) | | |
|---|---|---|---|---|
| | | Agent-17 | Comparative Experiment | Agent-13 |
| 7 | 100% Polyester | −1.0 | −11.0 | −3.0 |
| 8 | 100% Polyester | −1.75 | −9.0 | −1.0 |

What is claimed is:

1. A method for preparing a quaternary imidazoline salt comprising the steps of:

(a) contacting at reactive conditions essentially equimolar amounts of an imidazoline represented by the formula

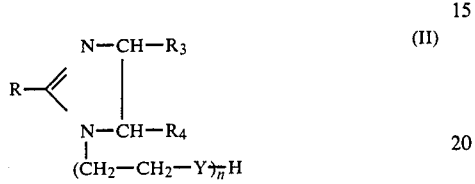

with an unsaturated carboxylic acid ester represented by the formula

so as to produce an imidazoline compound represented by the formula

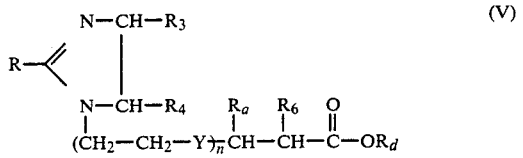

where in these formulas, R is an aliphatic, cycloaliphatic or aralkyl radical having up to 22 carbon atoms; $R_3$ and $R_4$ are each independently hydrogen, $C_1$-$C_4$ alkyl or $C_1$-$C_4$ hydroxyalkyl; Y is the divalent radical —O— or —NH—; n is the integer 0, 1 or 2, with the proviso that if n is 2, then Y is —NH—; $R_6$ is hydrogen or a $C_1$-$C_4$ alkyl; $R_a$ is hydrogen, methyl or

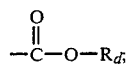

and $R_d$ is a $C_1$-$C_4$ alkyl;

(b) contacting at reactive conditions the imidazoline product represented by formula V with an essentially stoichiometric amount of an amine represented by the formula H—$NR_7R_8$, wherein $R_8$ is hydrogen or $C_1$-$C_4$ alkyl and $R_7$ is an aliphatic, cycloaliphatic or aralkyl radical having up to 22 carbon atoms, with the proviso that at least one of R and $R_7$ is a $C_8$-$C_{22}$ aliphatic radical, so as to amidate the

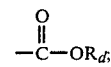

moieties borne by the imidazoline of formula V; and (c) contacting at reactive conditions the amidated imidazoline from step (b) with an essentially equimolar quantity of an alkylating agent selected from the group consisting of acrylic acid, methacrylic acid, methylchloride, ethylbromide, diethylsulfate, dimethylsulfate and hexadecylchloride to prepare a quaternary imidazolinium salt.

2. The process as described in claim 1 wherein R and $R_7$ are each independently an aliphatic radical having from 8 to 22 carbon atoms.

3. The process as described in claim 1 wherein $R_3$, $R_4$, $R_a$ and $R_8$ are each hydrogen and $R_6$ is hydrogen or methyl.

4. The process as described in claim 3 wherein n is 1.

5. The process as described in claim 3 wherein n is 1 and Y is the bivalent radical —O—.

6. The process as described in claim 1 wherein for step (a) the reaction temperature is maintained at less than 100° C.

* * * * *